United States Patent
Burek et al.

[11] Patent Number: 6,093,154
[45] Date of Patent: Jul. 25, 2000

[54] BIOPSY NEEDLE

[75] Inventors: Paul Burek, Aurora; Bonnie B. Vivian, Evergreen, both of Colo.; James Edney, Omaha, Nebr.

[73] Assignee: Denver Biomaterials, Inc., Golden, Colo.

[21] Appl. No.: 09/069,782

[22] Filed: Apr. 29, 1998

[51] Int. Cl.⁷ .................................................. A61B 10/00
[52] U.S. Cl. ........................ 600/564; 600/567; 606/167
[58] Field of Search .................................. 600/562, 564, 600/567; 606/167, 170, 181, 184, 185

[56] References Cited

U.S. PATENT DOCUMENTS

| | | | |
|---|---|---|---|
| 3,929,123 | 12/1975 | Jamshidi | 600/567 |
| 4,592,356 | 6/1986 | Gutierrez | 128/339 |
| 4,790,329 | 12/1988 | Simon | 600/567 |
| 4,799,495 | 1/1989 | Hawkins et al. | 600/567 |
| 4,931,059 | 6/1990 | Markham | 606/185 |
| 4,932,417 | 6/1990 | Ott | 600/570 |
| 4,953,558 | 9/1990 | Akerfeldt | 600/564 |
| 4,986,279 | 1/1991 | O'Neill | 600/567 |
| 5,158,565 | 10/1992 | Marcadis et al. | 600/567 |
| 5,573,008 | 11/1996 | Robinson et al. | 600/567 |

*Primary Examiner*—Cary O'Connor
*Assistant Examiner*—Charles Marmor, II
*Attorney, Agent, or Firm*—Peter F. Weinberg; Gibson, Dunn & Crutcher LLP

[57] ABSTRACT

A device for localizing and stabilizing a mass within the breast of a patient. The device has a housing with a sharpened cannula extending therefrom, and a plunger having a barbed wire extending therefrom that is slidably disposed within the housing. The barbed wire is releasable from the cannula housing by sliding the plunger, allowing the barb to engage a mass. A locking position prevents the plunger from unwanted sliding. Indicators alert a user as to the status of the device. The device can be held and used with one hand.

27 Claims, 4 Drawing Sheets

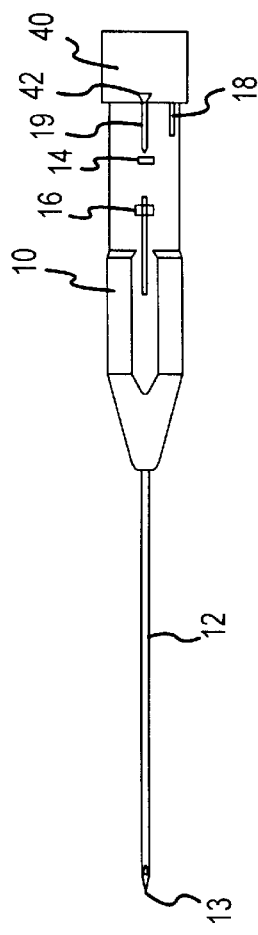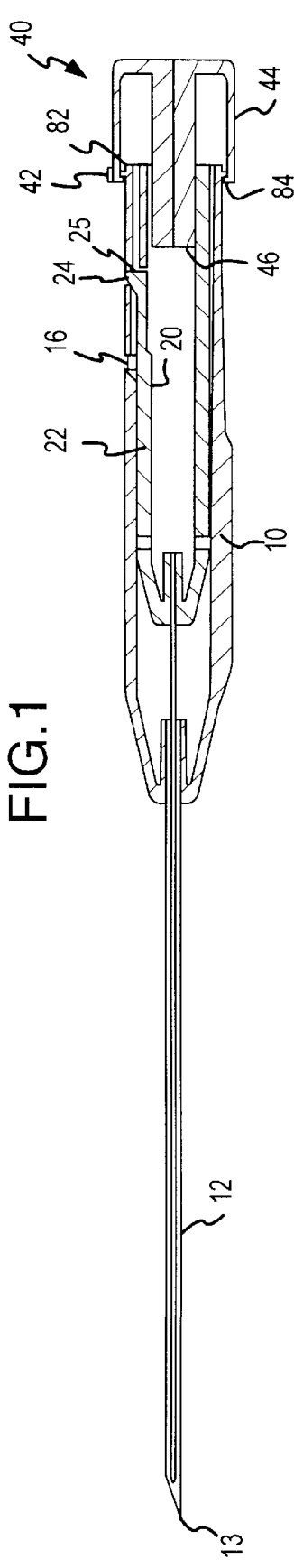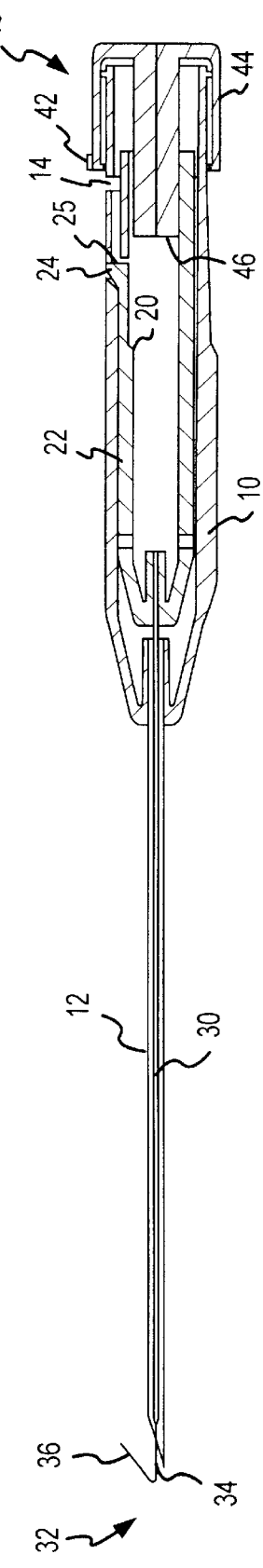

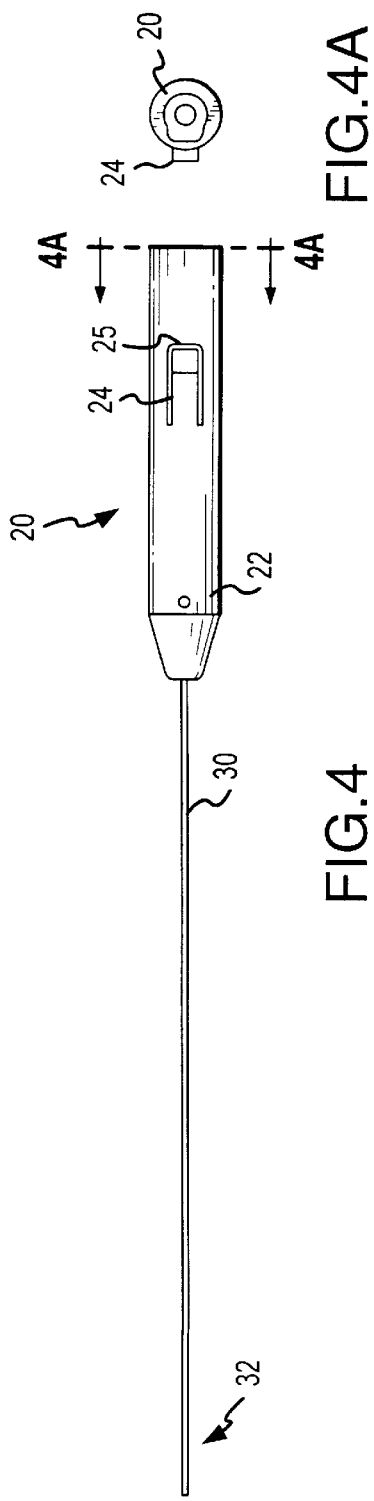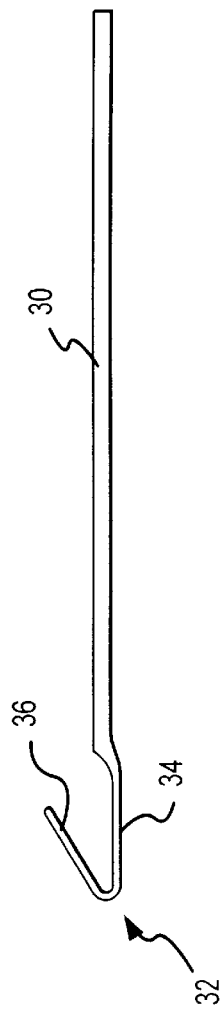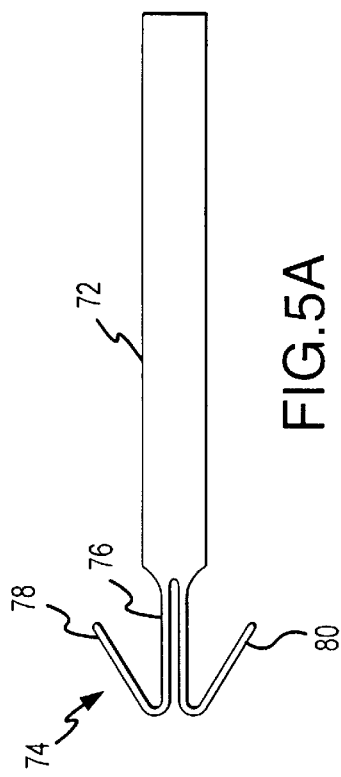
FIG.4A
FIG.4
FIG.5
FIG.5A

BIOPSY NEEDLE

FIELD OF THE INVENTION

The invention relates to the field of medical devices, and more particularly a device useful for the localization and removal of palpable masses from the breast of a patient.

BACKGROUND

A palpable mass (lump) may form within the breast of a subject. Such a mass is desirably removed, since it may metastasize if cancerous and endanger the health of the subject. In recent years, several hundred thousand breast surgery operations per year have been performed within the United States.

Although a large number of such operations have been performed, there is room for improvement in the relevant medical devices. A first step in such an operation is to localize (i.e., locate) the mass, in which step a device such as a Kopans Needle may be used. A Kopans Needle is a thin flexible needle with a looped end that is inserted through a separate cannula until the looped end engages the mass. A radiologist can then locate the Kopans Needle and mass. While a Kopans Needle or the like is useful for localizing a mass, it does not aid in the stabilizing of the mass and so does not aid in the removal of the mass. While many breast surgery operations do not pose any difficulties to the surgeon, in many other procedures it is difficult to grasp and isolate the mass.

A device that is able to locate and also stabilize a mass within a breast will assist surgeons in performing a mass removal procedure. More specifically, such a device will decrease the procedure time, reduce trauma to the breast tissue, reduce patient anxiety, and reduce unnecessary removal of healthy breast tissue. It should be understood that while breast surgery is intended use of the invention, it may also have use in other procedures requiring a mass to be localized and stabilized.

SUMMARY

The invention is a device to localize and grasp a mass to assist in the removal of such mass. A typical application of the device is to remove a mass during breast surgery.

In an embodiment, the invention is a device that has a housing with a sharpened cannula extending therefrom, and a plunger having a barbed wire member extending therefrom linearly disposed within the cannula. In a set position, the barb is contained within the cannula. In a deployed position, the barb extends from the cannula to localize and stabilize (grasp) a mass. The device also has locking position, wherein the barb is contained within the cannula as in the set position, but the barb cannot be deployed without first changing the device from the locking position to the set position.

The device has a cap engaged with the plunger, that can rotate and slide within the housing. Sliding the cap deploys the barb. The cap cannot be slid in the locked position. The cap is rotated by the user to change the device form the locking position to the set position. Indicators serve to indicate whether the device is in the locking position, set position, or deployed position.

The barb is preferably of a flattened material, to better grasp the mass as compared with a thin wire.

These and other features are described in detail below and with reference to drawings.

BRIEF DESCRIPTION OF THE DRAWINGS

FIG. 1 is a top exterior view of a device according to an embodiment of the invention, before the barb has been deployed.

FIG. 2 is a side section view of a device according to an embodiment of the invention, before the barb has been deployed.

FIG. 3 is a side section view of a device according to an embodiment of the invention, after the barb has been deployed.

FIG. 4 is an isolated top view of the plunger according to an embodiment of the invention.

FIG. 4A is end view of the plunger of FIG. 4.

FIG. 5 is a side view of the barb and wire member according to an aspect of the invention.

FIG. 5A is a side view of an alternative barb and wire member.

DETAILED DESCRIPTION

Figure 6:
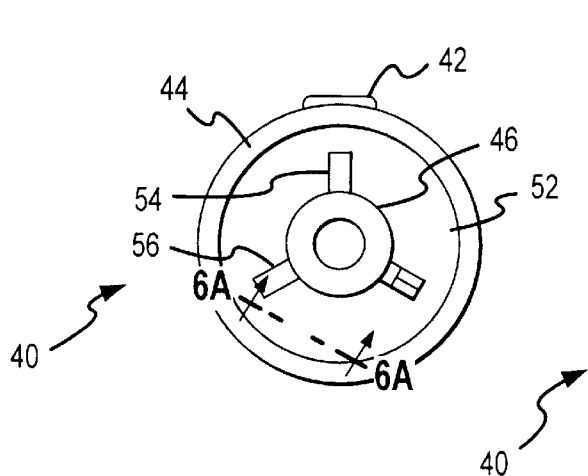
FIG. 6 is a distal end view of the cap according to an embodiment of the invention.

The invention is a device to assist in localizing and stabilizing a mass such as a palpable mass as may be found in the human breast. The device is useful in the surgical treatment, including the removal, of such a mass. A presently preferred embodiment of the invention is described, it being understood that such embodiment is for the purpose of illustrating the invention and not limiting the invention to the details described.

Referring now to FIGS. 1–3, the device includes a housing 10 having a rigid cannula tube 12 projecting distally from the housing. The rigid cannula 12 has a sharpened distal tip 13 suitable for insertion into a body. The rigid cannula 12 is fixedly attached to the housing 10, such as through insert molding or adhesive means. A preferable length of the portion of the cannula 12 extending beyond the housing is about 3 inches. A typical cannula 12 diameter is 16 gauge (having an outer diameter of about 0.065 inches and an inner diameter of about 0.056 inches).

The housing 10 houses a plunger 20. The plunger 20 is slidably disposed within the housing 10, so that it can be in a retracted position (as shown in FIG. 2) or in an advanced position (as shown in FIG. 3). The plunger 20 has a wire member 30 projecting distally from the plunger. The wire member 30 is slidably concentrically disposed within the cannula 12. The wire member is fixedly attached to the plunger 20, such as through insert molding or adhesive means.

The wire member 30 terminates distally at a barb 32. The wire member 30 and plunger 20 are sized so that in the plunger retracted position the barb 32 is contained within the cannula (FIG. 2), and in the plunger advanced position the barb extends beyond the cannula (FIG. 3). In the plunger retracted position, the device may be inserted into the breast of a patient, so this is termed the "set" position. In the plunger advanced position, the barb 32 can grasp and isolate a mass, so this is termed the "deployed" position.

The plunger 20 is operatively engaged to a cap 40. The cap 40 is linearly fixed in relation to the plunger 20 and linearly slidable in relation to the housing 10, so that a user can manipulate the cap to in turn manipulate the plunger. The cap 40 is configured so that a user may easily manipulate the cap with one hand while also holding the housing 10 with the same hand, thereby allowing the device to be used with only one hand. The cap 40 has a central post 46 that fits concentrically within the plunger 20 and housing 10, and is free to rotate within the plunger 20. The cap central post 46 attaches to a cap circumferential portion 44 that encircles at least a proximal portion of the housing 10.

As shown in FIG. 2, the cap includes an undercut 84 (which may be continuous or noncontinuous) that engages an annular rib 82 positioned on an outer proximal edge of the housing 10. The cap 40 snap-fits onto the housing 10 through the interface of the undercut 84 and rib 82, and the cap 40 is retained on the housing 10 through that interface.

The device includes an indicator feature to indicate whether the cap 40 is in the set position or the deployed position (as explained below, the device may also be in a separate locking position). The plunger 20 includes a primary plunger body 22 and a flexible beam 24 that extends away from the plunger body 22 (see also FIG. 4, showing an isolated top view of the plunger 20, and FIG. 4A, showing an end view). The housing 10 includes two indicator windows 14, 16 that are in line with each other, the window 16 being more distal than the window 14. In the set position, the beam 24 extends at least partially through the window 14, and is visible through the window 14. Preferably, the visible portion of the beam 24 is colored. As the plunger is slid from the set position to the deployed position, the beam 24 exits the window 14 and slides through the housing 10. When the plunger 20 reaches the deployed position, a portion of beam 24 extends through the window 16, and is visible through the window 16. The flexible beam 24 is under tension as it slides from the set position to the deployed position. This tension is at least partially relieved when the flexible beam extends partially through the windows. The tension and release of tension serves as a detent feature so that a user will feel when the plunger 20 is in either the set or deployed position, as opposed to being slid between the two positions, and positive force is required to move the plunger from the set position.

The plunger 20 is positively retained in the deployed position so that it cannot easily slide in relation in relation to the housing 10. The plunger 20 cannot move distally since the plunger would contact housing 10 if such motion were attempted (some slight play may be acceptable). The plunger cannot move proximally because the beam 24 is effectively locked in the window 16. The beam 24 preferably has a vertical proximal edge 25 (or is otherwise suitably shaped) to prevent the beam from being slid proximally once it is engaged with the window 16.

Another feature of the device is that it has a locking position. In the locking position, the cap 40 (and hence the plunger 20) cannot be slid through the housing 10, so the device will not be accidentally deployed. Before sliding the plunger 20, the cap 40 must be transferred from the locking position to the set position.

Figure 7:
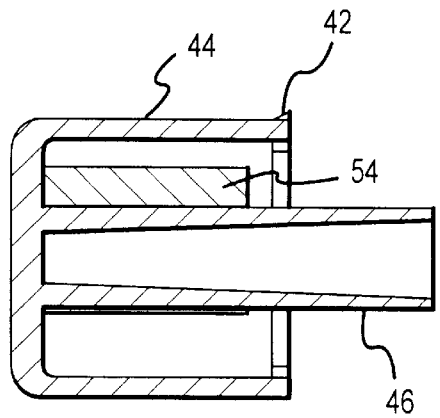
FIG. 7 is a side sectional view of the cap according to an embodiment of the invention.
Figure 8:
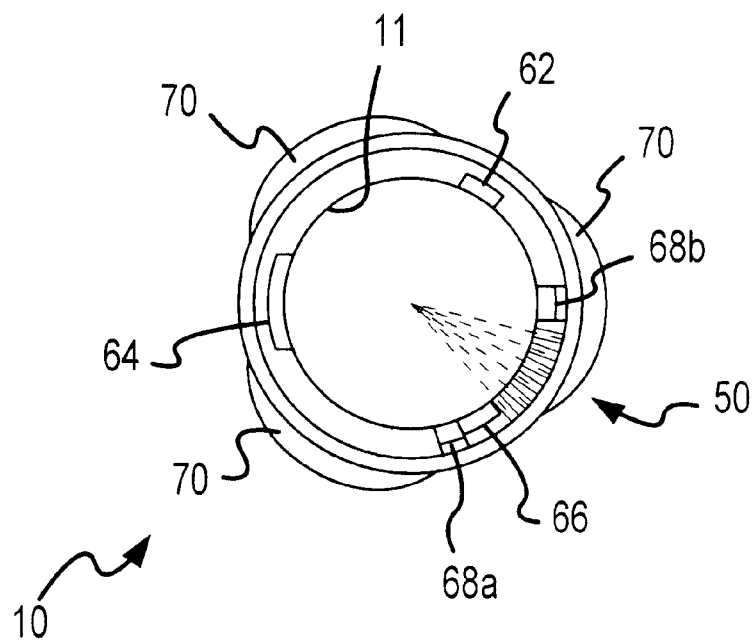
FIG. 8 is a proximal end view of the housing according to an embodiment of the invention.

The locking position preferably is accomplished by providing three tabs 52, 54, 56 on the cap 40 that can be aligned with three mating grooves 62, 64, and 66 formed within an interior surface 11 of the housing 10 (see FIGS. 6–8). The tabs project radially away from the cap post 46. If the tabs are not aligned with the grooves, the cap cannot be slid through the housing 10, as the tabs will be blocked by the proximal edge of the housing 10. If the tabs are aligned with the grooves, the cap can be slid though the housing as the tabs will slide through the grooves. While three tabs (spaced 120 degrees apart) are provided, it will be appreciated that more or fewer could be used, as is also the case with the grooves.

Preferably, the locking position includes a position that is about a one-quarter (more or less) circumferential turn away from the set position. The locking position is indicated by a marker 18 on the housing and a marker 42 on the cap 40 (see FIG. 1). In the locking position, the cap marker 42 is aligned with the housing marker 18. The cap 40 can be rotated until the cap marker 42 aligns with another maker 19 on the housing, which indicates the set position.

Figure 8A:
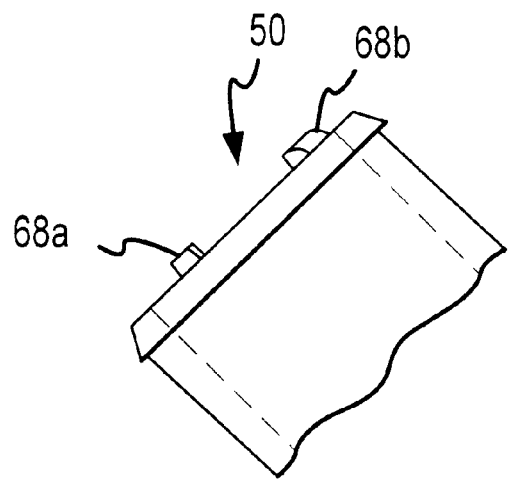
FIG. 8A is a detail view of the bumps and stops shown in FIG. 8.

The cap 40 and the housing 10 are rotatably engaged with each other via a ratchet mechanism (see FIG. 8). This provides a positive feel for the user as the cap 40 rotates, and also provides a threshold force that must be applied to rotate the cap. The ratchet mechanism includes a number of bumps 50 on a portion of the housing 10 that engages with one of the tabs (tab 52) of the cap 40. Preferably, about six bumps 50 are provided, although of course more or fewer could be used. The housing further includes stops 68a and 68b that are molded into a portion of the housing 10 that engages with one of the tabs (tab 52) of the cap 40. A stop 68a is adjacent one of the grooves (groove 66), so that the user is made aware (by tactile feel) of when the cap 40 is in the set position (i.e., when the tabs are aligned with the grooves, as tab 52 abuts the stop 68a). The bumps 50 and stops 68a, 68b are shown in the detail view of FIG. 8A.

Figure 6A:
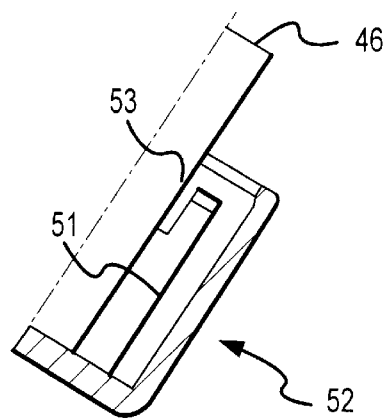
FIG. 6A is a detail view of one of the tabs according to the present invention.

With reference to FIG. 6A, a detail side view of tab 52 is provided. The tab 52 has an end portion 53 that has a greater width than an inner portion 51, so that the tab 52 has sufficient flexibility to ride over the bumps 50. The other tabs 54, 56 may have a constant width.

The wire member 30 and barb 32 is now described with reference to FIG. 5. The wire member is preferably made of a hollow needle such as a 25 gauge cannula (which has a diameter of 0.02 inches). A solid wire (of similar dimensions) could be used as an alternative. The barb has a section 34 that extends distally in line with wire member 30 (and hence the cannula 12). The barb has another section 36 that angles proximally toward the housing 10. An important aspect of the invention is that the barb sections 34 and 36 are flattened. Preferably, they have a width (the dimension perpendicular to the plane of the page the drawing in FIG. 5) of about 0.040 inches. This width allows the barb 32 to grab and isolate a mass without causing the mass to fragment and thus lose the grasp hold of the mass, as may be the case when using a Kopans Needle. Preferably, each section 34, 36 has a length of between about 0.187 and 0.250 inches, most preferably about 0.250 inches. The section 36 has a maximum perpendicular distance from the wire member 30 of about 0.08 inches (when deployed). The section 36 has sufficient metal memory so that it is contained within the cannula before deployment, and extends as shown in FIG. 5 when it is deployed from the cannula 12. The barb 32 is preferably formed by flattening an end portion of the wire member 30, and then bending the flattened end portion. Such a barb is particularly suited for grasping masses having a diameter of between about 0.5–3.0 cm.

An alternate wire member and barb are described with reference to FIG. 5A. Wire member 72 is preferably similar to wire member 30, namely a hollow tube of a small diameter. A solid wire (of similar dimensions) could be used as an alternative. Two barbs 74, 80 are formed on the distal end of wire member 72. Barb 74 has a section 76 that extends distally in line with the wire member 72 and another section 78 that angles proximally away so that a barb shape is provided. Both barbs are preferably flattened as described above in connection with barb 30, and have widths of about 0.040 inches for efficiently grasping and stabilizing a mass. The barbs may be formed from the same tube as wire member 72. This may be done by slicing an end of the tube 72 at two points so that two sections are formed, flattening each of the two sections, and bending each flattened section to form the two barbs. The ends are preferably bent in opposite directions so that the two barbs are 180 degrees apart from each other.

The housing of the device most preferably has a generally triangular cross-section, as shown in FIG. 8. This is accomplished by forming the molding so that is has three sections (denoted as 70) that protrude from the axis of the device. This improves the device ergonomics. Of course, the device could be formed with other shapes.

The operation of the device is now generally described. With the device preferably in the locking position, a surgeon will make an incision into the breast of a patient, and insert the sharpened end 13 of the cannula into the breast until it is proximate a mass to be removed (i.e., at or through the mass). The device is placed into the set position by twisting the cap until the cap marker 42 aligns with the housing marker 19. The barb is then deployed by pressing the cap 40 while holding the housing 10 fixed. This causes the barb 30 to insert within or around the mass (to be determined by the positioning of the cannula with respect to the mass, at the preference of the surgeon). At this point, the mass is localized by barb. If desired, the surgeon could remove his or hand from the device, and the mass remains localized and stabilized by the device. When the surgeon is ready to remove the mass, the surgeon can use the cannula 12 as a guide to place the scalpel (or other removal device) to the proper site for removal, and in particular can draw the scalpel along the length of the cannula until the scalpel is at the site of the mass. The device can be used to manipulate the position of the mass with respect to the surrounding tissue. In this way, the mass can be positioned so that the removal of healthy tissue is minimized.

It should be appreciated that a number of features of the invention have been described, but it is not necessary to include each and every feature into a useful device.

What is claimed is:

1. A device for the localization and stabilization of a mass within a body, comprising:
    a housing having a cannula fixedly projecting distally therefrom; a plunger having a wire member having a barb fixedly projecting distally therefrom, the plunger being slidably disposed within said housing when the device is in a set position such that the wire member is slidably disposed within the cannula and the barb is contained within the cannula;
    the plunger being slidable from the device set position to a device deployed position wherein the barb extends beyond the cannula and is capable of grasping the mass; a cap that is linearly fixedly attached to the plunger, and slidably and rotatably attached to the housing; wherein the device has a locking position wherein the cap and plunger cannot slide in relation to the housing when the device is in the locking position; and wherein the cap is rotatable within the housing from the set position to the locking position.

2. The device of claim 1, wherein the cap has at least one tab that can be aligned with at least one groove in the housing, whereby the device is in the set position when the tab is aligned with the groove and the device is in the locking position when the tab is not aligned with the groove.

3. The device of claim 2, wherein the cap is attached to the housing via a ratchet mechanism, whereby at least a threshold force is required to rotate the cap with respect to the housing.

4. The device of claim 3, wherein the ratchet mechanism comprises a series of bumps on the housing that engage the at least one cap tab.

5. The device of claim 4, wherein the at least one cap tab engaging said bumps is flexible.

6. The device of claim 5, wherein the housing has at least one stop that indicates when the cap is rotated into the set position and prevents further rotation of the cap beyond the set position.

7. The device of claim 2, wherein the cap extends proximally beyond the housing.

8. The device of claim 7 wherein the cap engages the housing at a snap fit interface.

9. The device of claim 8, wherein at least a portion of the cap has a substantially circular cross section encircling the housing.

10. The device of claim 9, wherein the cap includes an inner post that extends into the plunger.

11. The device of claim 1, further comprising a visual indicator to indicate whether the device is in the locking position or the set position; wherein the visual indicator includes two markers on the housing and a marker on the cap, wherein the cap marker aligns with one of the housing markers in the set position and the other of the housing markers in the locking position.

12. The device of claim 11, wherein the housing marker indicating the set position is larger than the housing marker indicating the locking position.

13. The device of claim 11, further comprising a visual indicator to indicate whether the device is in the set position or in the deployed position.

14. The device of claim 13, wherein the visual indicator includes at least one window on the housing and at least one marker on the plunger.

15. The device of claim 14, wherein the at least one window on the housing includes a first window and second window, wherein the plunger marker is visible though the first window when the device is in the set position and the marker is visible through the second window when the device is in the deployed position.

16. The device of claim 15, wherein the plunger includes a plunger body and an engagement member extending from the plunger body that engages the housing.

17. The device of claim 16, wherein the plunger engagement member is a flexible beam and the plunger marker is a portion of the flexible beam.

18. The device of claim 17, wherein the beam provides a tactile detent as the plunger is slid from the set position to the deployed position.

19. The device of claim 18, wherein the tactile detent is provided by a portion the beam fitting into the second indicator window formed on the housing.

20. The device of claim 19, wherein the beam portion fitting into the indicator window is the indicator and is colored whereby its visibility is enhanced.

21. The device of claim 19, wherein the beam fitting into the second indicator window produces an audible click.

22. The device of claim 19, wherein the beam fitting into the second indicator window prevents the plunger from being slid proximally with respect to the housing.

23. A device for the localization and stabilization of a mass within a body, comprising:

a housing having a cannula fixedly projecting distally therefrom;

a plunger having a wire member having a barb fixedly projecting distally therefrom;

means for locking said plunger with respect to said housing wherein said barb is contained within said cannula such that linear force on the device does not affect the position of the barb;

means for unlocking said plunger with respect to said housing into a set position wherein linear force on the device deploys the barb from the cannula into a deployed position; and means for preventing the barb from being retracted within the cannula after the barb is deployed.

24. A method of making a device for the localization and stabilization of a mass within a body, comprising:

establishing a housing having a cannula fixedly projecting distally therefrom;

slidably disposing a plunger having a wire member having a barb fixedly projecting distally therefrom, such that when the device is in a set position the wire member is slidably disposed within the cannula and the barb is contained within the cannula;

wherein the plunger is slidable from the device set position to a device deployed position wherein the barb extends beyond the cannula and is capable of grasping the mass;

making the barb flat from a single hollow tube from which the wire member is also made, such that the barb has a first section that extends distally in-line within the cannula and the barb has a second section that angles proximally towards the housing.

25. The method of claim 24, wherein the step of making the barb includes flattening an end of said tube a flattened section, and bending said flattened section to from the first barb section and the second barb section.

26. The method of claim 25, wherein said single tube is substantially a 25 gauge cannula.

27. A method of making a device for the localization and stabilization of a mass within a body, comprising:

establishing a housing having a cannula fixedly projecting distally therefrom;

slidably disposing a plunger having a wire member having a barb fixedly projecting distally therefrom, such that when the device is in a set position the wire member is slidably disposed within the cannula and the barb is contained within the cannula;

wherein the plunger is slidable from the device set position to a device deployed position wherein the barb extends beyond the cannula and is capable of grasping the mass;

wherein the barb is a first barb and further comprising a second barb substantially similar to the first barb, the barbs extending from the wire member at 180 degree angle relative to each other;

making the barbs by slicing an end of a single hollow tube in a direction along the tube axis, the slicing occurring at two radial positions, flattening the sliced end of the tube into two flattened sections, and bending said two flattened section to form the first and second barbs.

* * * * *